United States Patent [19]
Murugan et al.

[11] Patent Number: 5,932,736
[45] Date of Patent: Aug. 3, 1999

[54] PREPARATION OF HETEROCYCLES USING 1,3-DIHALOPROPENES

[75] Inventors: Ramiah Murugan, Indianapolis; Eric F. V. Scriven, Greenwood, both of Ind.

[73] Assignee: Reilly Industries, Inc., Indianapolis, Ind.

[21] Appl. No.: 09/056,681

[22] Filed: Apr. 7, 1998

Related U.S. Application Data

[60] Provisional application No. 60/042,738, Apr. 7, 1997.
[51] Int. Cl.$^6$ .................. C07D 213/06; C07D 213/08; C07D 213/09
[52] U.S. Cl. .................. 546/250; 546/251; 546/330; 546/336; 546/345; 544/180
[58] Field of Search ....................... 546/250, 251

[56] References Cited

U.S. PATENT DOCUMENTS

| | | | |
|---|---|---|---|
| 4,784,243 | 11/1988 | Beck et al. ................. | 548/202 |
| 5,180,833 | 1/1993 | Uneme et al. ............... | 548/202 |
| 5,705,652 | 1/1998 | Jackson et al. ............. | 548/202 |

FOREIGN PATENT DOCUMENTS

| | | | |
|---|---|---|---|
| 0 763 531 | 3/1997 | European Pat. Off. ...... | C07D 277/32 |
| 0 794 180 | 9/1997 | European Pat. Off. ...... | C07D 277/32 |
| WO 96/16050 | 5/1996 | WIPO .................... | C07D 277/24 |

OTHER PUBLICATIONS

K. Schulze, F. Richter, R. Weisheit, R. Krause, M. Muhlstadt, M. Muhlstadt, "Zur Darstellung und Charakterisierung von Vinylsenfolen", Journal F. prakt. Chemie, Band 322, Heft 4, 1980, S. 629–637 (1980).

A.K. Mukerjee and R. Ashare, "Isothiocyanates in the Chemistry of Heterocycles", Chemical Reviews, vol. 91, No. 1, pp. 1–24 (Jan./Feb. 1991).

*Primary Examiner*—Alan L. Rotman
*Attorney, Agent, or Firm*—Woodard, Emhardt, Naughton Moriarty & McNett

[57] ABSTRACT

Described are preferred processes for preparing heterocycles having one or more nitrogen and/or oxygen heteroatoms, utilizing a 1,3-dihalopropene as an effective 3-carbon fragment. Preferred processes yield pyridines, quinolines, oxazoles, pyrimidines and pyrazoles, depending upon the other reactant or reactants utilized with the 1,3-dihalopropene.

29 Claims, No Drawings

PREPARATION OF HETEROCYCLES USING 1,3-DIHALOPROPENES

REFERENCE TO RELATED APPLICATION

This application claims priority upon U.S. patent application Ser. No. 60/042,738, filed Apr. 7, 1997, which is hereby incorporated herein by reference in its entirety.

BACKGROUND OF THE INVENTION

The present invention relates generally to the preparation of heterocycles containing one or more nitrogen or oxygen heteroatoms, and in particular to the synthesis of such heterocycles utilizing a 1,3-dihalopropene such as 1,3-dichloropropene as 4 starting material.

As further background, heterocyclic compounds such as pyridines, pyrimidines, oxazoles, pyrazoles and quinolines enjoy a wide range of utilities including serving as actives and intermediates in the fields of herbicidal, pesticidal, and medicinal compounds. While many such compounds occur naturally and in the past have been isolated from natural sources, currently, most of the world's supply of such compounds derives from synthetic preparations. Thus, a wide variety of syntheses are known in which one or more acyclic starting materials are reacted either to directly form the heterocycles or to form cyclizable intermediates which can then be converted to the heterocycles.

In light of this background the applicants have undertaken an investigation to discover new and useful routes to the above-mentioned heterocycles which employ readily-available starting materials and which can be conveniently conducted in standard laboratory or commercial equipment. In so doing the applicants have discovered that 1,3-dihalopropenes provide useful 3-carbon fragments for the production of such heterocycles including, for instance, 2,3-substituted pyridines, 2,5-substituted pyridines, pyrimidines, oxazoles, pyrazoles and quinolines.

SUMMARY OF THE INVENTION

Accordingly, in one broad aspect, the invention provides for the use of a 1,3-dihalopropene in the production of a heterocycle containing one or more nitrogen or oxygen heteroatoms, including for example pyridines, quinolines, pyrimidines, pyrazoles and oxazoles.

In broad aspects the invention thus provides a process for preparing a heterocycle having one or more nitrogen or oxygen heteroatoms, comprising reacting a 1,3-dihalopropene compound of the formula:

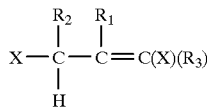

wherein X is halo, $R_1$ is H or $R_4$ wherein $R_4$ is H or a straight chain lower alkyl or benzyl group, and $R_2$ and $R_3$ are each H or a straight chain lower alkyl or benzyl group, with:

(1) acrylonitrile so as to form a cyclizable intermediate, and then cyclizing said intermediate to form a corresponding 2-halo-5-substituted pyridine compound, with the proviso that $R_1$ is H;

(2) a compound of the formula CN—$CH_2$—$R_5$ wherein $R_5$ is $COOR_6$, CN, $CON(R_6)_2$, or $COR_6$, wherein $R_6$ is H or an alkyl, aryl or aralkyl group having 1 to about 10 carbon atoms, so as to form a cyclizable intermediate, and then cyclizing said intermediate to form a corresponding 2-halo-3-substituted-pyridine compound;

(3) a compound of the formula $H_2N$—$NHR_7$ wherein $R_7$ is H or an alkyl, aryl or aralkyl group having up to about 10 carbon atoms, so as to form a cyclizable intermediate; and then cyclizing said intermediate to form a corresponding pyrazole compound;

(4) hydroxylamine so as to form a cyclizable intermediate, and then cyclizing said intermediate to form a corresponding oxazole compound;

(5) a compound of the formula $H_2N$—CZ—$NH_2$ wherein Z is O, S or NH, so as to form a cyclizable intermediate, and then cyclizing said intermediate to form a corresponding pyrimidine;

(6) an aniline compound of the formula

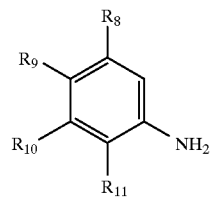

wherein $R_8$, $R_9$, $R_{10}$ and $R_{11}$ are each H or an alkyl, aryl or aralkyl group having up to about ten carbon atoms, so as to form a corresponding N-(3-halo-2-propenyl)aniline compound, and then cyclizing the an N-(3-halo-2-propenyl) aniline compound to form a corresponding quinoline compound; or (7) a compound of the formula CN—$XC^-$—$R_5$ wherein X is halo, $R_5$ is $COOR_6$, CN, $CON(R_6)_2$, or $COR_6$, wherein $R_6$ is H or an alkyl, aryl or aralkyl group having 1 to about 10 carbon atoms, so as to form a cyclizable intermediate, and then cyclizing said intermediate to form a corresponding 2-halo-3-substituted-pyridine.

One specific, preferred embodiment of the invention provides a process for preparing a 2-halo-5-(methyl or halomethyl)-pyridine which includes the step of reacting a 1,3-dihalopropene with acrylonitrile to form a cyclizable intermediate compound, and cyclizing the intermediate compound to form the indicated 2,5-substituted pyridine. In one preferred mode of carrying out this process, the cyclization can be conducted in the presence of a halogenating agent, and the product is a 2-halo-5-halomethyl-pyridine. In another preferred mode, the cyclization is conducted in the absence of the halogenating agent, and the product is a 2-halo-5-methyl-pyridine. In addition, the 1,3-dihalopropene starting material can be substituted with additional groups to form further substituted pyridines. For example, provided by the present invention are processes for preparing a 2-halo-5-substituted-pyridines which include reacting a 1,3-dihalopropene of the formula

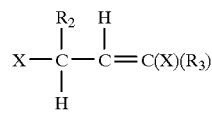

wherein X is halo and $R_2$ and $R_3$ are each H or a lower alkyl or benzyl group, with acrylonitrile so as to form a cyclizable intermediate. The intermediate is then cyclized to form a 2-halo-5-substituted-pyridine of the formula:

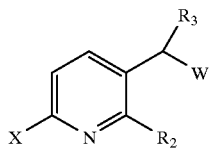

wherein X, $R_2$ and $R_3$ are as defined above, and W is H or halo. In particular, where the cyclization is conducted in the presence of a halogenating agent, W will be halo. Where the cyclization is conducted in the absence of a halogenating agent, W will be H.

Another specific preferred embodiment of the invention provides a process for forming a pyrimidine of the formula

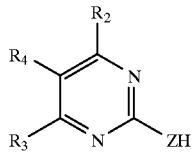

wherein Z is O, S, or NH, and $R_2$, $R_3$ and $R_4$ are each H or a straight chain lower alkyl or benzyl group, which includes reacting a compound of the formula

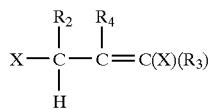

wherein X is halo and $R_2$, $R_3$ and $R_4$ are as defined above, with a compound of the formula $H_2N$—$CZ$—$NH_2$ wherein Z is as defined above, so as to form a cyclizable intermediate, and then cyclizing the intermediate to form the pyrimidine. As examples, X can be O providing urea as a starting material, which can be used in conjunction with the 1,3-dihalopropene to prepare 2-hydroxy-pyrimidines. In a corresponding synthesis, thiourea (X=S) can be used to prepare 2-sulfhydryl-pyrimidines. In still further syntheses, guanidine (X=NH) can be used to prepare 2-amino-pyrimidines.

In another specific preferred embodiment of the invention, a process is provided for preparing a 2-halo-3-substituted pyridine. In this process, a 1,3-dihalopropene is reacted with a compound of the formula NC—$CH_2$—$R_5$, wherein $R_5$=$COOR_6$, CN, $CON(R_6)_2$, or $COR_6$, wherein $R_6$ is H or an alkyl, aryl or aralkyl group having 1 to about 10 carbon atoms, to form a 2-halo-5-$R_5$-pyridine.

In the area of pyrazoles, the invention provides a specific preferred embodiment for the preparation of a pyrazole of the formula

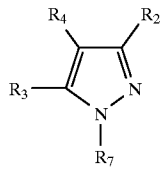

by reacting a compound of the formula $H_2N$—$NHR_7$ wherein $R_7$ is H or an alkyl, aryl or aralkyl group having up to about ten carbon atoms, with a compound of the formula

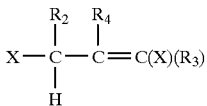

wherein X is halo and $R_2$, $R_3$ and $R_4$ are each H or a straight chain lower alkyl or benzyl group, to form a cyclizable intermediate, and cyclizing the intermediate to form the pyrazole.

In the field of quinolines, in accordance with a specific preferred embodiment of the invention, quinolines can be prepared by reacting an aniline of the formula

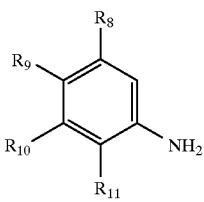

wherein $R_8$, $R_9$, $R_{10}$ and $R_{11}$ are each H or an alkyl, aryl or aralkyl group having up to about ten carbon atoms, with a compound of the formula

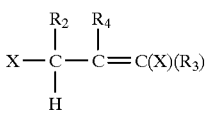

wherein X is halo and $R_2$, $R_3$ and $R_4$ are each H or a straight chain lower alkyl or benzyl group, to form an N-(3-halo-2-propenyl)aniline of the formula

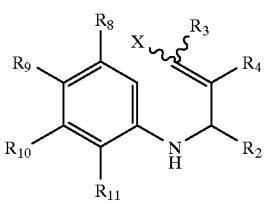

wherein X, $R_2$, $R_3$, $R_4$, $R_8$, $R_9$, $R_{10}$ and $R_{11}$ are as defined above. This aniline can in turn be cyclized to form a quinoline of the formula

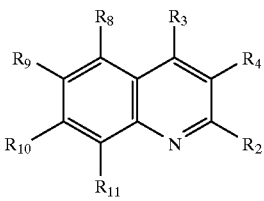

wherein $R_2$, $R_3$, $R_4$, $R_8$, $R_9$, $R_{10}$ and $R_{11}$ are as defined above.

In still another specific preferred embodiment, the invention provides a for preparing a 2-halo-3-substituted-pyridine, which includes reacting a 1,3-dihalopropene of the formula

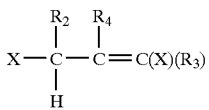

wherein X is halo and $R_2$, $R_3$ and $R_4$ are each H or a lower alkyl or benzyl group, with a compound of the formula $CN-XC^--R_5$ wherein X is halo, $R_5$ is $COOR_6$, CN, $CON(R_6)_2$, or $COR_6$, wherein $R_6$ is H or an alkyl, aryl or aralkyl group having 1 to about 10 carbon atoms, so as to form a cyclizable intermediate; and cyclizing said intermediate to form a 2-halo-3-substituted-pyridine compound of the formula:

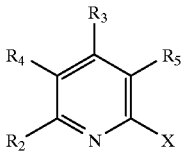

wherein X, $R_2$, $R_3$, $R_4$ and $R_5$ are as defined above.

The invention thus provides processes for preparing a variety of heterocycles having one or more nitrogen or oxygen heteroatoms utilizing readily-available 1,3-dihalopropenes as starting materials, which are reacted with other available starting materials to form the heterocycles. The preferred reactions can be conducted in standard equipment under relatively mild conditions. In addition, processes of the invention involve starting materials which are relatively easy to transport, store and manipulate.

Additional objects, features and advantages of the invention will be apparent from the following description and appended claims.

DESCRIPTION OF THE PREFERRED EMBODIMENTS

For the purpose of promoting an understanding of the principles of the invention, reference will now be made to certain preferred embodiments thereof and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

As indicated above, the present invention provides for the production of heterocyclic compounds including a nitrogen or oxygen heteroatom, utilizing a 1,3-dihalopropene starting material as an effective three-carbon fragment. In processes of the invention, either two or three carbons from the 1,3-dihalopropene starting material are incorporated into the heterocyclic ring. For instance, the 1,3-dihalopropene, a 1,3-electrophile, can be reacted with a 1,3-nucleophile so that three carbons from the 1,3-dihalopropene are incorporated into a heterocyclic ring, e.g. in the synthesis of 2-halo-3-substituted pyridines, pyrazoles, oxazoles, and quinolines as described herein. In other reactions, the 1,3-dihalopropene is reacted with another compound, and the formed intermediate cyclized in the presence of a halogenating agent, wherein two carbons of 1,3-dihalopropene starting material are incorporated into the heterocyclic ring, and the third carbon is advantageously incorporated as a substituent on the ring, for instance in the synthesis of certain 2-halo-5-substituted pyridine compounds as described herein. These reactions, particularly in those cases wherein 3 carbons of the 1,3-dihalopropene are incorporated into the heterocyclic ring, can be conducted in the presence of a catalyst which facilitates the nucleophilic displacement, for example a palladium catalyst such as a ligated palladium zero complex.

Preferred processes of the invention generally include the steps of reacting a 1,3-dihalopropene compound of the formula

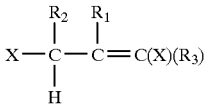

wherein X is halo such as chloro, bromo or iodo, $R_1$ is H or $R_4$ wherein $R_4$ is H or a straight chain lower alkyl or benzyl group, and $R_2$ and $R_3$ are each H or a straight chain lower alkyl or benzyl group, with a second reactant, optionally in the presence of a catalyst as discussed above, to form an intermediate cyclizable to form the desired heterocyclic compound. The intermediate is then cyclized to form the desired heterocyclic compound. In these regards, this 1,3-dihalopropene starting material can be a cis- or trans-isomer, or a mixture of such isomers, and any intermediates formed can likewise have cis- or trans-configurations, or a mixture thereof.

Each of the reactions involved in the syntheses described herein can be conducted for any suitable time to yield the desired product, typically up to about 20 hours, more preferably up to about 10 hours. The halogenating agent, when used, can include any suitable source of halogen, including for example molecular halogen and compounds which dehalogenate under the reaction conditions, e.g. a sulfuryl halide which dehalogenates to produce molecular halogen. Preferred halogenating agents include those which provide molecular chlorine, molecular bromine and/or molecular iodine, most preferably molecular chlorine. In one preferred form, gaseous chlorine can be fed to and reacted with a liquid reaction mixture to form the desired compound.

Reactions in accordance with the invention are preferably conducted in an organic solvent, although they also may be conducted neat. Preferred solvents are aprotic solvents, with illustrative solvents including cyclic or acyclic ethers, including dioxanes, cyanoalkanes, e.g. acetonitrile and proprionitrile, ethyl acetate, and the like.

As disclosed above, 1,3-dihalopropenes (optionally further substituted with hydrocarbon groups) provide effective reactants in the synthesis of a variety of heterocyclic compounds containing one or more nitrogen and/or oxygen heteroatoms. In particular, Table 1 and Schemes 1–7 below illustrate preferred syntheses of the present invention. Specifically, Table 1 shows preferred Additional Reactants (other than the 1,3-dihalopropene also included), preferred Solvents, and preferred Reaction Temperatures which can be used, and the preferred Products classes which are formed. Schemes 1–7 show expected intermediates and final products resulting from the reaction of the Additional Reactants shown in Table 1 with a 1,3-dihalopropene. In Schemes 1–7, $R_2$, $R_3$, and $R_4$ are generally H, straight chain lower alkyl ($C_1$ to $C_6$ alkyl) groups, or benzyl groups; $R_8-R_{11}$ are each H or an alkyl, aryl or aralkyl group having up to about ten carbon atoms; and the remainder of the variables are as defined in Table 1. In addition, the usage is the Schemes and elsewhere herein of the wave-line (∿) denotes a carbon bond in which no particular stereochemistry is intended (i.e. the compound can be cis-, trans- or a mixture of cis- and trans-isomers), and the usage of the symbol [O] denotes oxidative conditions, for example as can be achieved in the presence of a suitable oxidizing agent such as a peroxide, e.g. hydrogen peroxide, nitric acid, manganese dioxide, permanganate, a chromium compound, and/or an oxygen-rich environment. These and other expedients, for example the use of appropriate catalysts for the reactions as described herein, will be within the purview of those skilled in the area.

TABLE 1

| Additional Reactants | Solvents | Reaction Temperatures | Products |
|---|---|---|---|
| Acrylonitrile + HX[a] (see Scheme 1) | Non-Protic (e.g. 1,3-DHP[b]) | 20° C.–100° C. | 2-halo-5-methylpyridine |
| NC—CH$_2$—R$_5$[c] + HX[a] (see Scheme 2) | Non-Protic (e.g. 1,3-DHP[b]) | 50° C.-reflux (~100° C.) | 2-halo-3-substituted pyridines |
| NC—C$^-$X[a]—R$_5$[c] (see Scheme 3) | Non-Protic (e.g. Ethyl Acetate) | ~20° C.-100° C. | 2-halo-3-substituted pyridines |
| H$_2$N—CZ[d]—NH$_2$ (see Scheme 4) | Non-Protic (e.g. 1,3-DHP[b]) | ~50° C.-reflux (~100° C.) | 2-substituted pyrimidines |
| H$_2$N-NHR$_7$[e] (see Scheme 5) | Non-Protic (e.g. 1,3-DHP[b]) | ~50° C.-reflux (~100° C.) | Pyrazoles |
| Hydroxylamine (see Scheme 6) | Non-Protic (e.g. 1,3-DHP[b]) | ~50° C.-reflux (~100° C.) | Oxazole |
| Anilines (see Scheme 7) | (1) Non-Protic (e.g. acetonitrile); (2) Aqueous Acid (e.g. 80% H$_2$SO$_4$) | (1) ~50° C.-reflux (~100° C.); (2) ~120° C.–145° C. | Quinolines |

[a]X = halogen (Cl, Br, I).
[b]1,3-DHP = the 1,3-dihalopropene reactant (e.g. in excess).
[c]R$_5$ = COOR$_6$, CN, CON(R$_6$)$_2$, or COR$_6$, wherein R$_6$ is H or an alkyl, aryl or aralkyl group having 1 to about 10 carbon atoms.
[d]Z = O, S or NH.
[e]R$_7$ = H or an alkyl, aryl or aralkyl group having up to about ten carbon atoms

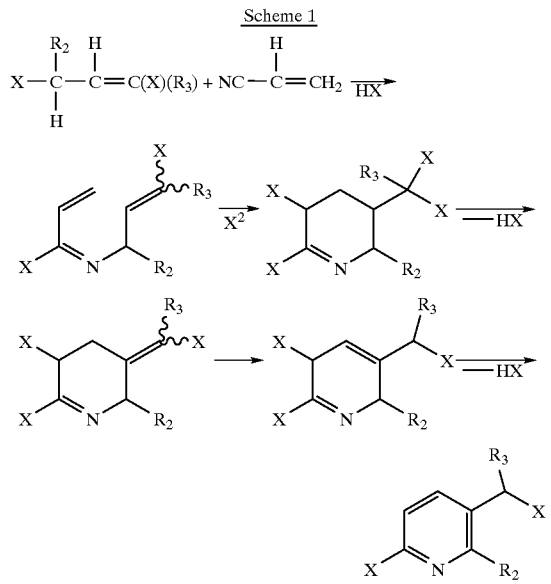

Scheme 1

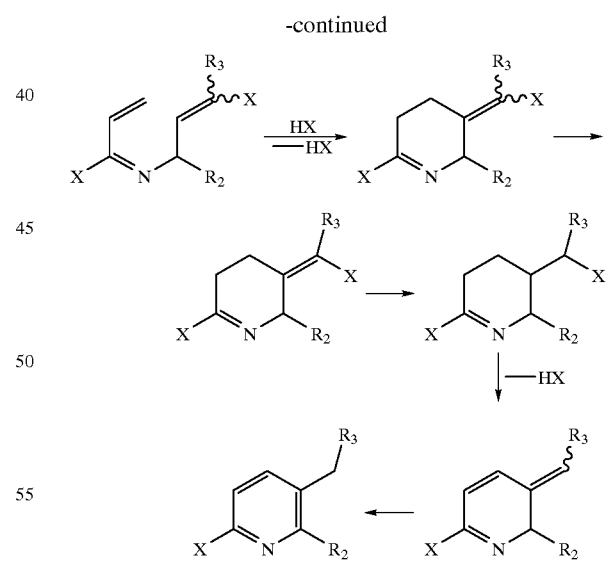

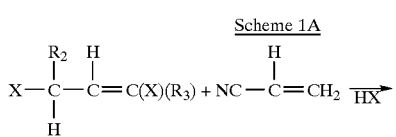

Scheme 1A

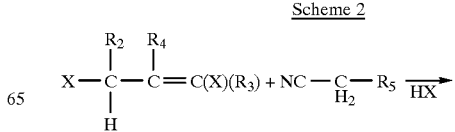

Scheme 2

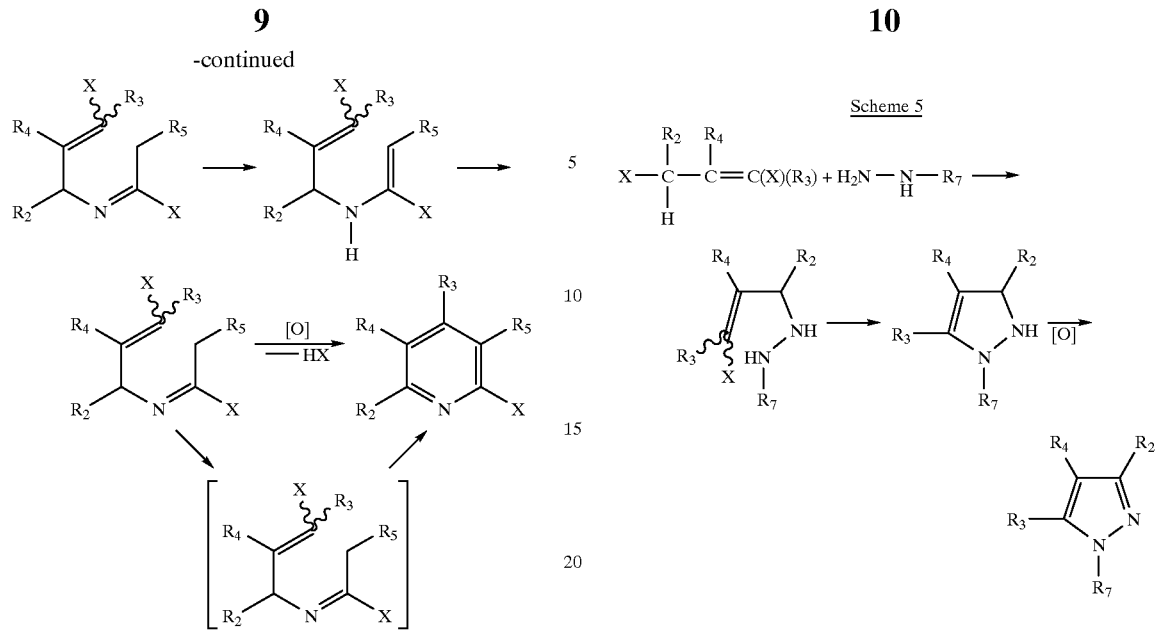
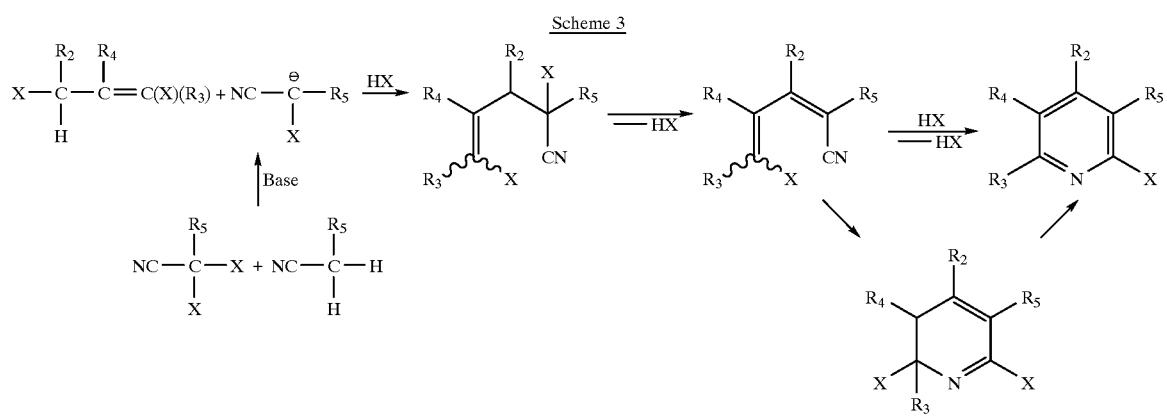
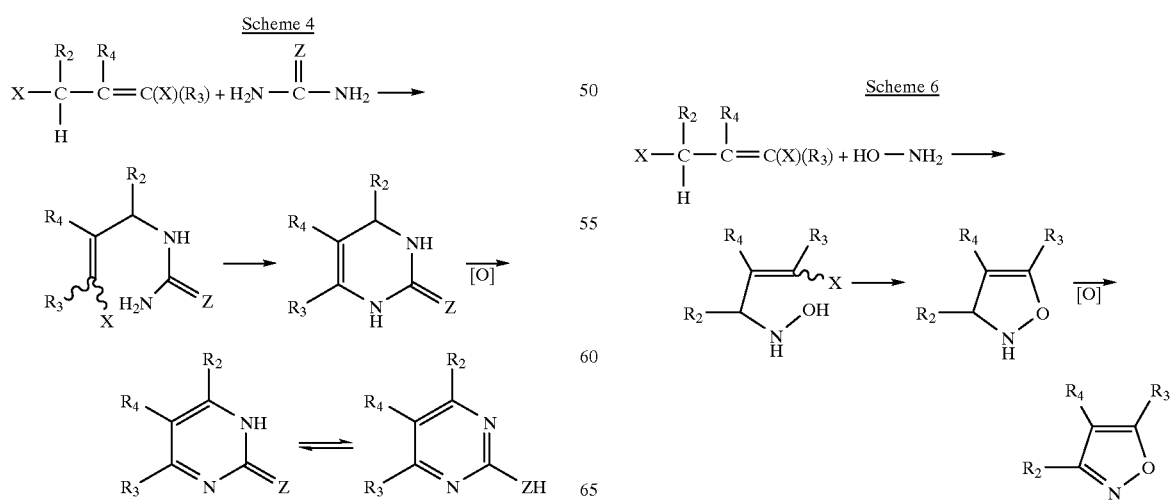

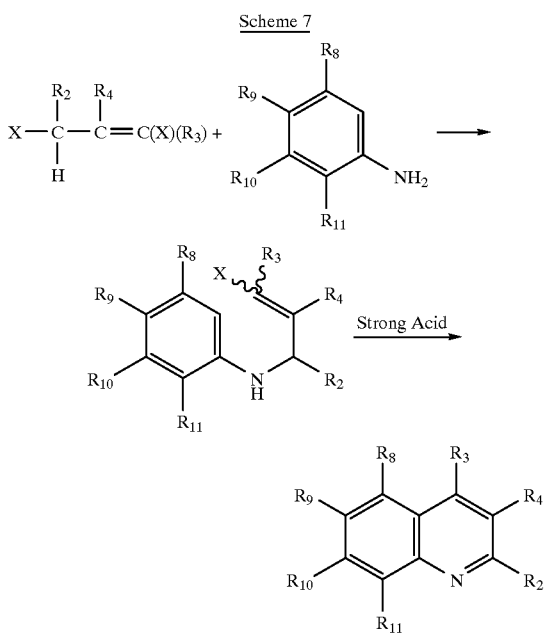

Scheme 7

The heterocycle products of the invention are generally useful as active agents or as intermediates to active agents employed in pesticidal, herbicidal and/or medicinal compositions. As specific examples, 2-chloro-3-substituted pyridines such as 2-chloronicotinic acid are used as intermediates to a variety of agrochemicals, including herbicides, as well as medicinal compounds such as enzyme inhibitors.

For the purposes of promoting a further understanding and appreciation of the invention and its various advantages, the following specific Examples are given. It will be understood, however, that these Examples are illustrative, and not limiting, in nature.

EXAMPLE 1

Preparation of N-(3-chloro-2-propenyl)aniline 1 mole of aniline was dissolved in 200 mL acetonitrile, and 0.7 mole 1,3-dichloropropene was added. The reaction was heated to reflux overnight with mechanical stirring. The reaction was then filtered and concentrated. Upon distillation, N-(3-chloro-2-propenyl)aniline was obtained as a yellow solid. The main distillation cut contained 65% N-(3-chloro-2-propenyl)aniline by weight.

EXAMPLE 2

Cyclization of N-(3-chloro-2-propenyl)aniline to form Quinoline 0.12 g of sodium iodide were added to 10 g of the N-(3-chloro-2-propenyl)aniline product of Example 1. 33 g of 80% sulfuric acid were then added slowly. The reaction was exothermic. After the addition, the reaction mix was heated to 140° C. by distilling water from the reaction using a Dean Stark column. The reaction was heated for 3 hours at 120° C. to 145° C. The reaction was then neutralized with 25% sodium hydroxide to a pH of 8, while controlling temperature with an ice bath. The reaction mix was extracted with toluene to recover the quinoline, which was confirmed by NMR and GC analysis.

The invention has been described above with reference to preferred embodiments thereof. It will be understood that various modifications and additions can be made to the specific embodiments disclosed without departing from the spirit and scope of the invention, and all such modifications and additions are contemplated as being a part of the present invention. In addition, all publications cited herein are indicative of the level of skill in the art, and are hereby incorporated by reference as if each had been individually incorporated by reference and fully set forth.

What is claimed is:

1. A process for preparing a 2-halopyridine compound, comprising reacting a 1,3-dihalopropene compound of the formula:

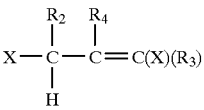

wherein X is halo, $R_4$ is H or a straight chain lower alkyl or benzyl group, and $R_2$ and $R_3$ are each H or a lower alkyl or benzyl group, with:

(1) acrylonitrile so as to form a cyclizable intermediate, and then cyclizing said intermediate so as to form a 2-halo-5-substituted-pyridine of the formula:

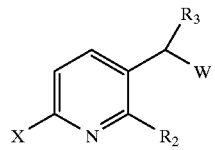

with the proviso that $R_4$ is H, and wherein X, $R_2$ and $R_3$ are as defined above, W is H when said cyclizing is conducted in the absence of a halogenating agent, and W is halo when said cyclizing is conducted in the presence of a halogenating agent; or (2) a compound of the formula $CN-CH_2-R_5$ wherein $R_5$ is $COOR_6$, CN, $CON(R_6)_2$, or $COR_6$, wherein $R_6$ is H or an alkyl, aryl or aralkyl group having 1 to about 10 carbon atoms, so as to form a cyclizable intermediate, and then cyclizing said intermediate to form a corresponding 2-halo-3-substituted-pyridine compound of the formula:

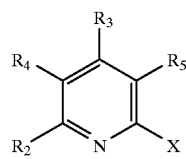

wherein X, $R_2$, $R_3$, $R_4$ and $R_5$ are as defined above; or (3) a compound of the formula $CN-XC^--R_5$ where X is halo, $R_5$ is $COOR_6$, CN, $CON(R_6)_2$, or $COR_6$, wherein $R_6$ is H or an alkyl, aryl or aralkyl group having 1 to about 10 carbon atoms, so as to form a cyclizable intermediate, and then cyclizing said intermediate to form a corresponding 2-halo-3-substituted-pyridine compound of the formula:

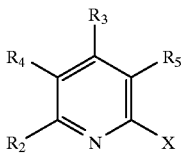

wherein X, $R_2$, $R_3$, $R_4$ and $R_5$ are as defined above.

2. A process according to claim 1, for forming a 2-halo-5-methylpyridine compound, which comprises:
reacting a 1,3-dihalopropene of the formula

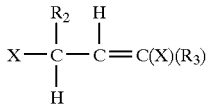

wherein X is halo and $R_2$ and $R_3$ are each H or a lower alkyl or benzyl group, with acrylonitrile so as to form a cyclizable intermediate; and
cyclizing said intermediate so as to form a 2-halo-5-substituted-pyridine of the formula:

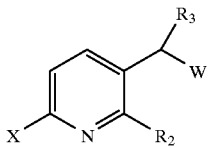

wherein X, $R_2$ and $R_3$ are as defined above, and W is H or halo.

3. The process of claim 2 wherein said cyclizing is in the presence of a halogenating agent, and wherein W is halo.

4. The process of claim 2 wherein said cyclizing is in the absence of a halogenating agent, and wherein W is H.

5. A process according to claim 1, for preparing a 2-halo-3-substituted-pyridine, comprising:
reacting a 1,3-dihalopropene of the formula

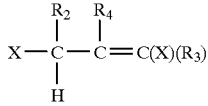

wherein X is halo and $R_2$, $R_3$ and $R_4$ are each H or a lower alkyl or benzyl group, with a compound of the formula CN—$CH_2$—$R_5$ wherein $R_5$ is $COOR_6$, CN, $CON(R_6)_2$, or $COR_6$, wherein $R_6$ is H or an alkyl, aryl or aralkyl group having 1 to about 10 carbon atoms, so as to form a cyclizable intermediate; and
cyclizing said intermediate to form a 2-halo-3-substituted-pyridine compound of the formula:

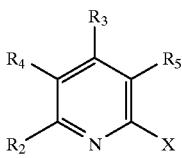

wherein X, $R_2$, $R_3$, $R_4$ and $R_5$ are as defined above.

6. The process of claim 5 wherein the 1,3-dihalopropene is 1,3-dichloropropene, X is Cl, and $R_2$, $R_3$, and $R_4$ are each H.

7. The process of claim 6 wherein $R_5$ is COOR.

8. The process of claim 7 wherein $R_5$ is COOH.

9. A process according to claim 1, for preparing a 2-halo-3-substituted-pyridine, comprising:
reacting a 1,3-dihalopropene of the formula

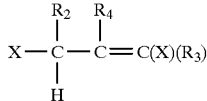

wherein X is halo and $R_2$, $R_3$ and $R_4$ are each H or a lower alkyl or benzyl group, with a compound of the formula CN—$XC^-$—$R_5$ wherein X is halo, $R_5$ is $COOR_6$, CN, $CON(R_6)_2$, or $COR_6$, wherein $R_6$ is H or an alkyl, aryl or aralkyl group having 1 to about 10 carbon atoms, so as to form a cyclizable intermediate; and
cyclizing said intermediate to form a 2-halo-3-substituted-pyridine compound of the formula:

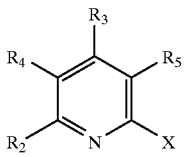

wherein X, $R_2$, $R_3$, $R_4$ and $R_5$ are as defined above.

10. The process of claim 1, wherein said cyclizing is conducted under heat, or in the presence of acid, or both.

11. The process of claim 2, wherein $R_2$ and $R_3$ are each H or a lower alkyl group.

12. The process of claim 11, wherein $R_2$ and $R_3$ are each H.

13. The process of claim 2, which comprises reacting 1,3-dichloropropane with acrylonitrile in the presence of hydrogen halide to form a cyclizable intermediate, and cyclizing said intermediate in the presence of a halogenating agent to form a 2-halo-5-halomethylpyridine, or in the absence of a halogenating agent to form a 2-halo-5-methylpyridine.

14. The process of claim 13, wherein said cyclizing is conducted in the presence of halogenating agent to form a 2-halo-5-halomethylpyridine.

15. The process of claim 14, wherein said halogenating agent is or provides molecular chlorine, molecular bromine, or molecular iodine.

16. The process of claim 15, wherein said halogenating agent is or provides molecular chlorine.

17. The process of claim 5, wherein $R_2$, $R_3$ and $R_4$ are each H or a lower alkyl group.

18. The process of claim 17, wherein $R_5$ is $COOR_6$ wherein $R_6$ is H or and alkyl group.

19. The process of claim 17, wherein $R_5$ is CN.

20. The process of claim 17, wherein $R_5$ is $CON(R_6)_2$ wherein $R_6$ is H or an alkyl group.

21. The process of claim 17, wherein $R_5$ is $COR_6$ wherein $R_6$ is H or an alkyl group.

22. The process of claim 5, wherein X is chloro, bromo, or iodo.

23. The process of claim 22, wherein X is chloro.

24. The process of claim 9, wherein $R_2$, $R_3$ and $R_4$ are each H or a lower alkyl group.

25. The process of claim 24, wherein $R_5$ is $COOR_6$, wherein $R_6$ is H or an alkyl group.

26. The process of claim 24, wherein $R_5$ is CN.

27. The process of claim 24, wherein $R_5$ is $CON(R_6)_2$, wherein $R_6$ is H or an alkyl group.

28. The process of claim 9, wherein X is chloro.

29. The process of claim 9, wherein the 1,3-dihalopropene is 1,3-dichloropropene.

* * * * *